United States Patent [19]

Simpson

[11] Patent Number: 5,152,742
[45] Date of Patent: Oct. 6, 1992

[54] SWAB APPARATUS

[75] Inventor: Ian Simpson, Monroe, Conn.

[73] Assignee: Euroceltique, S.A., Luxembourg

[21] Appl. No.: 680,438

[22] Filed: Apr. 4, 1991

[51] Int. Cl.⁵ .......................................... A61M 35/00
[52] U.S. Cl. ...................................................... 604/3
[58] Field of Search ........................................ 604/1-3

[56] References Cited

U.S. PATENT DOCUMENTS

| | | | |
|---|---|---|---|
| 3,757,782 | 9/1973 | Aiken | 604/3 |
| 3,958,571 | 5/1976 | Bennington | 604/3 |
| 3,981,304 | 9/1976 | Szpur | 604/3 |
| 4,148,318 | 4/1979 | Meyer | 604/3 |
| 4,329,990 | 5/1982 | Sneider | 604/2 |
| 4,498,796 | 2/1985 | Gordon et al. | 604/3 X |
| 4,747,719 | 5/1988 | Parking | 604/3 X |
| 4,854,760 | 8/1989 | Pike et al. | 604/3 X |

Primary Examiner—David J. Isabella
Assistant Examiner—Elizabeth M. Burke
Attorney, Agent, or Firm—Steinberg & Raskin

[57] ABSTRACT

Swab apparatus for use in topical application of treatment materials comprise a swab, a flexible-walled container having an interior in which a quantity of treatment material is situated, and a coupling tube having a forward end portion to which the swab is connected and a rearward end portion coupled to the container, for placing the swab and the treatment material within the container into fluid communication with each other.

1 Claim, 3 Drawing Sheets

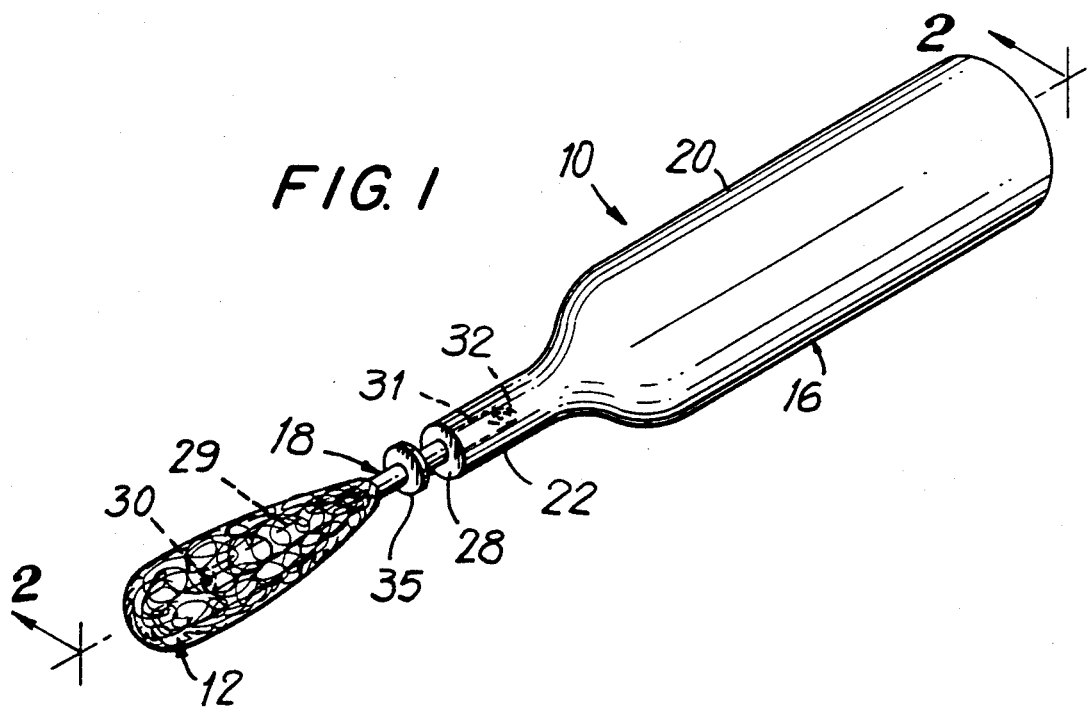
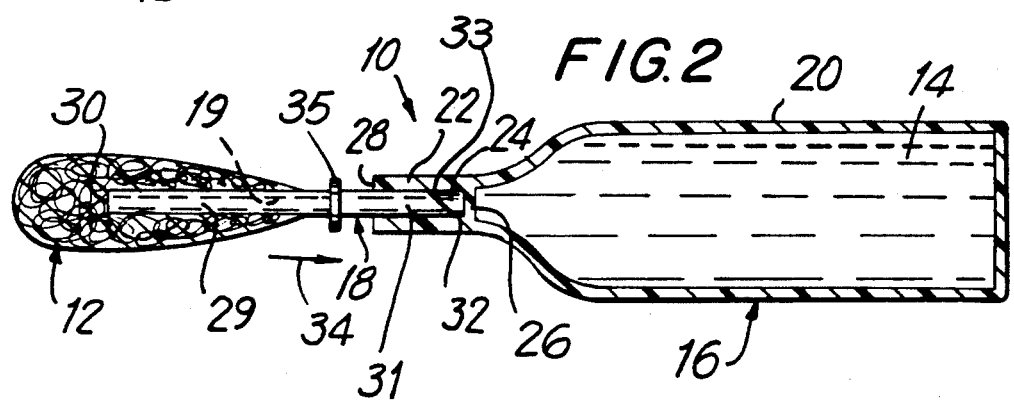
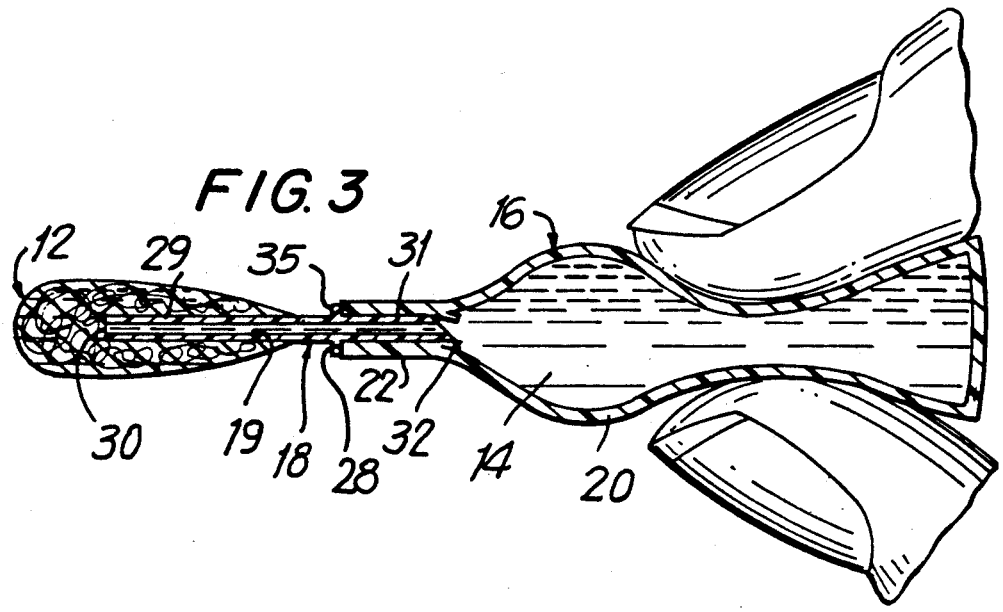

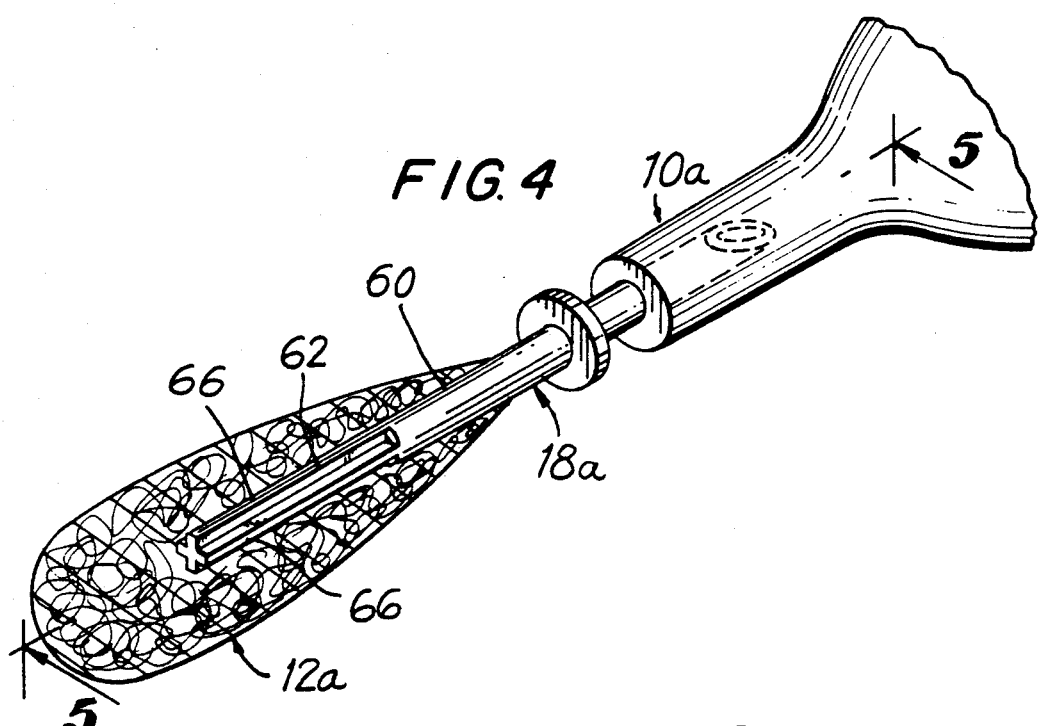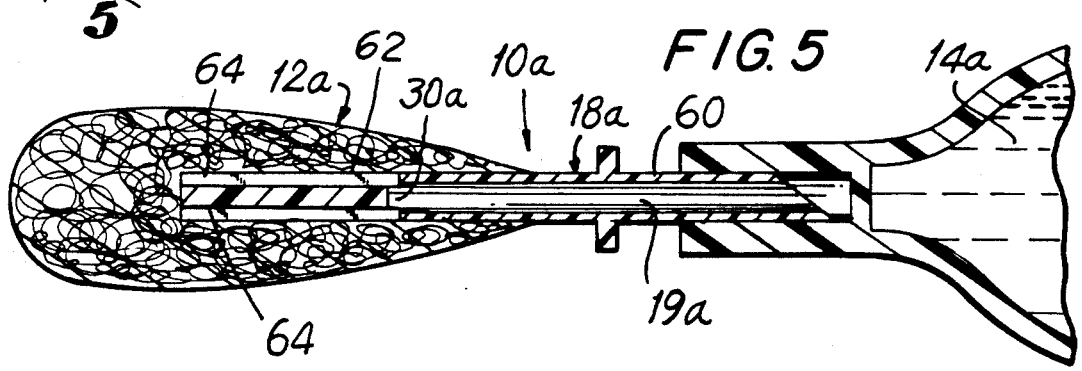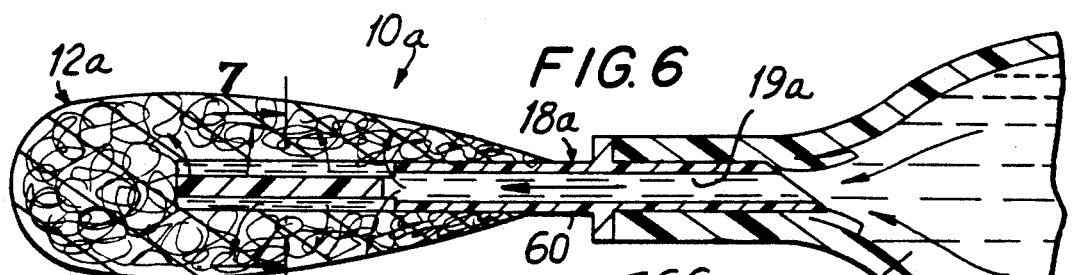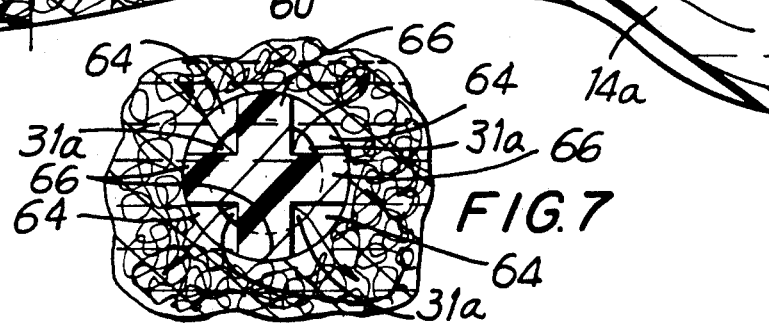

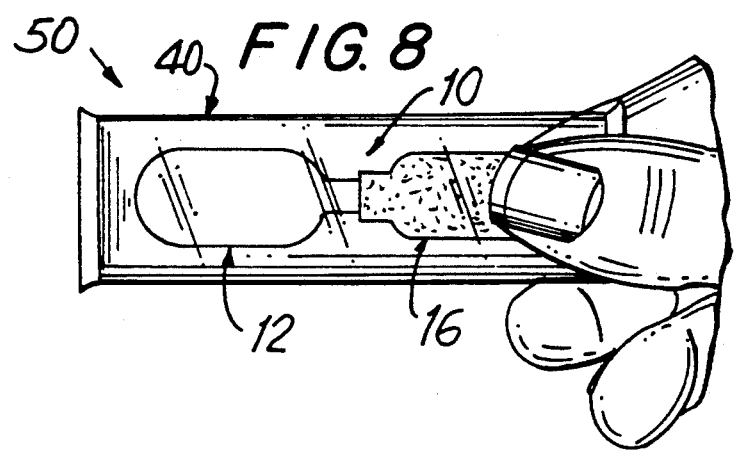
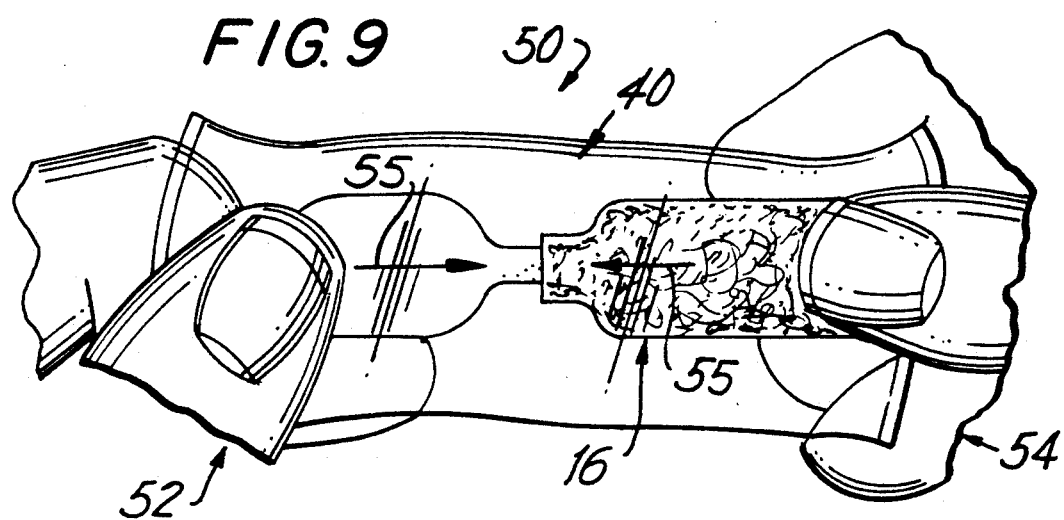
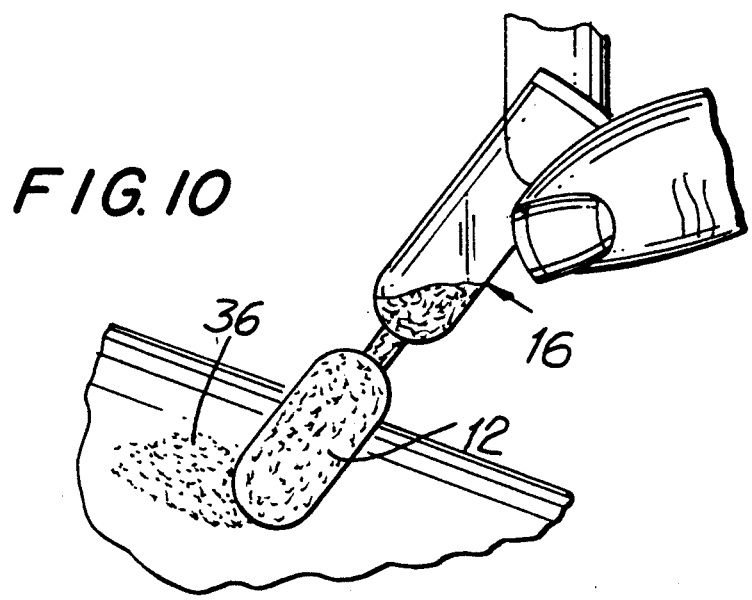

5,152,742

SWAB APPARATUS

BACKGROUND OF THE INVENTION

This invention relates generally to swab apparatus and, more particularly, to swab apparatus for use in the topical application of treatment materials.

Swab devices are well known and generally comprise an elongate, stick-like handle to the end of which a cotton swab is attached. While grasping the device by the handle, the swab is immersed in a container of desired treatment material, such as an antiseptic solution, a local anesthetic or the like, or the treatment material may be poured onto the swab. The swab is then rubbed over the area to be treated to apply the treatment material. The swab may be re-dipped in the treatment material as necessary.

The conventional swabbing technique described above is not entirely satisfactory for the simple reason that one of either the swab device or the container of treatment material may not be readily available when needed, since they are normally stored separately from each other. Moreover, the supply of treatment material may have been depleted from previous usage making it difficult or impossible to dip the swab into the material.

SUMMARY OF THE INVENTION

It is an object of the present invention to provide new and improved swab apparatus for use in the topical application of treatment materials.

Another object of the present invention is to provide new and improved swab apparatus comprising a swab device integrated with a reservoir of treatment material.

Still another object of the present invention is to provide new and improved swab apparatus incorporating a sealed supply of treatment material and in which dispensing the treatment material onto the swab is accomplished in a controlled manner.

Yet another object of the present invention is to provide new and improved swab apparatus in which treatment material is dispensed onto the swab uniformly over its length.

A further object of the present invention is to provide new and improved swab apparatus having a construction adapted for economical production and sale to justify disposal after a single use.

Briefly, in accordance with the present invention, these and other objects are attained by providing swab apparatus comprising a swab, a reservoir of treatment material sealed in a flexible-walled container, and coupling means which, upon activation of the apparatus, provides a passage between the interior of the container and the swab, thereby enabling the treatment material to flow in a controlled manner from the container to impregnate the swab.

In a preferred embodiment, the container comprises a main body portion formed of flexible plastic sheet material which narrows at one of its ends to an elongated, reduced diameter, sleeve-like port integral with the body portion. A thin, puncturable membrane is formed within the port inwardly of its open end and normally seals the treatment material within the interior of the body portion of the container. The swab is attached to one end portion of a coupling tube, while the other free end portion of the coupling tube is situated and snugly held within the sleeve-like port of the container forwardly of the sealing membrane. To activate the swab apparatus, the coupling tube is forced further into the port of the container until it punctures the sealing membrane so that the coupling means provides a passage for the treatment material from the container to the swab. Treatment material is dispensed into the swab in a controlled manner, by squeezing the container to a desired degree, forcing the treatment material to flow from the container, through the coupling means, and into the swab, whereupon the swab becomes impregnated with treatment material. The discharge end of the coupling means may be formed to define at least one axial channel into which the treatment material flows whereby the swab becomes impregnated with treatment material substantially uniformly. The supply of treatment material on the swab can be replenished as required. The container functions as a handle for the swab apparatus during the subsequent application of the treatment material.

DESCRIPTION OF THE DRAWINGS

A more complete appreciation of the present invention and many of the attendant advantages thereof will be readily obtained as the same becomes better understood by reference to the following detailed description when considered in connection with the accompanying drawings in which:

FIG. 1 is a perspective view of swab apparatus in accordance with the invention:

FIG. 2 is a section view taken along line 2—2 of FIG. 1, illustrating the swab apparatus in its pre-activated condition;

FIG. 3 is a view similar to FIG. 2 illustrating the swab apparatus in its activated condition, as treatment material is being dispensed from the container onto the swab;

FIG. 4 is a partial perspective view of another embodiment of swab apparatus in accordance with the invention in which the treatment material is dispensed into the swab uniformly over a part of its length;

FIG. 5 is a section view taken along line 5—5 of FIG. 4 illustrating the swab apparatus in its pre-activated condition;

FIG. 6 is a view similar to FIG. 5 illustrating the swab apparatus in its activated condition, as treatment material is being dispensed from the container onto the swab;

FIG. 7 is a section view taken along line 7—7 of FIG. 6;

FIG. 8 is a schematic view illustrating an assembly including swab apparatus in accordance with the invention in packaged form;

FIG. 9 illustrates activation of the swab apparatus of the assembly shown in FIG. 8; and FIG. 10 is a perspective view illustrating use of the swab apparatus of the invention in the topical application of treatment material.

DESCRIPTION OF THE PREFERRED EMBODIMENTS

Referring now to the drawings wherein like reference characters designate identical or corresponding parts throughout the several views, and more particularly to FIGS. 1 and 2, swab apparatus in accordance with the invention, generally designated 10, comprises a cotton swab 12, a reservoir of treatment material 14, such as an antiseptic solution, sealed in a container 16, and coupling means including a hollow pipette-like coupling tube 18 having an axial bore 19 which, upon activation of the apparatus in the manner described below, provides a passage between the interior of container 16 and swab 12 through which treatment material 14 flows from the container to impregnate the swab. Coupling tube 18 may be formed of metallic or plastic sheet material, and is illustrated herein as formed of plastic.

Container 16 is formed of flexible transparent plastic sheet material, and comprises a tube-like body portion 20 closed at one of its ends. The other end of the container 16 narrows and merges into an elongate, reduced diameter sleeve-like port 22, integral with body portion 20, defining an inner bore 24. A thin, puncturable membrane 26 (FIG. 2) is formed within bore 24 of port 22 inwardly of its open end 28. Membrane 26 seals the treatment material 14 within the interior of the body portion 20 of container 16.

Swab 12 is attached to a forward end portion 29 of coupling tube 18 so that the corresponding forward end of the coupling tube bore 19, which comprises a discharge opening 30, is situated in the central interior of the swab. A rearward end portion 31 of coupling tube 18 is situated and snugly held within the bore 24 of port 22 forwardly of the sealing membrane 26. The outer diameter of coupling tube 18 is substantially equal to, or slightly greater than, the diameter of the port bore 24, so that the coupling tube 18 is reliably held within the port 22 by a friction fit. Prior to use, such as during storage, the coupling tube 18 is in an outer, pre-activated position with respect to container 16. More particularly, prior to activation, the end 32 of the coupling tube 18, which is bevelled to present a sharp point, is in an outer, non-activated position situated forwardly of membrane 26 so that the reservoir of treatment material 14 contained within the body portion 20 of container 16 remains sealed within it.

Referring now to FIG. 3 in conjunction with FIGS. 1 and 2, in order to activate the swab apparatus, coupling tube 18 is shifted in the direction of arrow 34 (FIG. 2) further into the bore 24 of port 22, so that its pointed end 32 punctures membrane 26. The rearward end 33 of the coupling tube bore 19 thus opens into the interior of the container body portion 20. Coupling tube 18 is provided with a stop member 35 positioned to limit the extent to which the rearward end portion 31 of coupling tube 18 can be forced into the container. In particular, when the open end 33 of the coupling tube bore 19 reaches the point at which the container walls start to diverge to form the body portion 29 (FIG. 3), stop member 35 abuts against the end 28 of the container port 22, thereby preventing further inward movement.

In use, after the swab apparatus has been activated as described above the body portion of container 16 is squeezed as shown in FIG. 3 to force a quantity of treatment material 14 into and through the bore 19 of coupling tube 18 from which it flows out from discharge opening 30 to impregnate swab 12. As seen in FIG. 10, using the container 16 as a handle, the impregnated swab is then stroked over the region 36 to be treated to apply the treatment material thereto. The supply and replenishment of treatment material to the swab is controlled by further pressure on the container.

Referring to FIGS. 4-7, an embodiment of the invention is illustrated in which the swab is impregnated with treatment material substantially uniformly over its length so that the entire swab may become impregnated faster than in the case of the embodiment discussed above and shown in FIGS. 1-3. In that embodiment, the treatment material is discharged from the discharge opening 30 of bore 19 into the forward ends of the swab 12 which therefore becomes saturated with the treatment material before the end of the swab. As seen in the embodiment of FIGS. 4-7, in which features that correspond to those of the embodiment of FIGS. 1-3 are designated by the same reference numeral with the suffix "a", the swab apparatus 10a comprises a cotton swab 12a, a reservoir of treatment material 14a sealed in a container 16a, and coupling means 18a. The components of swab apparatus 10a have substantially the same construction as the swab apparatus 10. However, the coupling means 18a differs in construction in that it comprises a coupling tube part 60 having an axial bore 19a, and a coaxial material discharge part 62 defining four external channels 64 communicating with the opening end 30a of bore 19a.

The channels 64 are formed by four radial ribs 66 integral with the tube part 60 of coupling member 18a. The discharge part 62 extends longitudinally through the swab 12 over a portion of its length. In the manufacture of the swab apparatus, the swab is connected or formed on the coupling member in a conventional manner such that the channels 64 remain unobstructed by swab material, as best seen in FIG. 5. In use, treatment material 14a flows through bore 19a and into the four channels 64 through the respective open segments 31a (FIG. 7) of the bore discharge opening 30a.

As seen in FIG. 6 the treatment material tends to flow through the entire length of channels 64 whereupon further compression of the container 16a causes the treatment material to move in a radial direction as shown by arrows 68 into the swab along the length of the swab. In this manner, the entire swab is impregnated with treatment material in a uniform manner.

A preferred embodiment for packaging swab apparatus in accordance wit the invention is illustrated in FIGS. 8 and 9. As seen in FIG. 8, swab apparatus 10 comprising swab 12 coupled to container 16 in pre-activated form, is packaged in a transparent plastic envelope 40 sealed at both of its ends, to form a packaged swab assembly, generally designated 50. Unit packaging of this type is advantageous in that the swab apparatus can be activated while the envelope 40 remains sealed so that the fingers need not come into contact with the treatment material. Thus, referring to FIG. 9, the swab 12 is grasped through envelope 40 with one hand 52 while the container 16 is grasped through envelope 40 by the other hand 54. The swab apparatus 10 is activated by pushing the swab and container toward each other in the directions of arrows 55 to puncture the sealing membrane as described above. The treatment material is preferably dispensed onto the swab 12 before opening envelope 40 by squeezing the container 16 through the envelope 40. The envelope 40 is opened and the swab apparatus is grasped by the container and removed from the envelope ready for use. In this manner, the fingers of the user need not ever come into contact with the treatment material.

It will be understood that the particular shapes of the swab and container are not restricted to those illustrated in the drawings and that any desired treatment material may be used, so long as it is flowable. For example, dilute solutions as well as relatively viscous substances may be utilized in conjunction with the invention.

Obviously, numerous modifications and variations of the present invention are possible in the light of the above teachings. It is therefore to be understood that within the scope of the claims appended thereto, the invention may be practiced otherwise than as specifically disclosed herein.

What is claimed is:

1. Swab apparatus for topical application of treatment material, comprising a swab;

a flexible-walled container having an interior in which a quantity of treatment material is situated;

sealing means for sealing said interior of said container with said treatment material therewith; and selectively operable coupling means for placing said swab and said treatment material situated within said container interior into fluid communication with each other, said coupling means comprising at least one longitudinally extending channel, said channel comprised of a tube part and a discharge part including at least one longitudinally extending channel, said discharge part extending forwardly from said tube-part coaxially thereof, and said longitudinally extending channel of said discharge part being divided into at least a pair of oppositely facing longitudinally extending channels.

* * * * *